United States Patent
McNeff et al.

(10) Patent No.: US 9,107,941 B2
(45) Date of Patent: Aug. 18, 2015

(54) METHODS AND COMPOSITIONS FOR REDUCING L-PIPECOLIC ACID EFFECTS IN ANIMALS

(75) Inventors: Clayton V. McNeff, Andover, MN (US); Larry C. McNeff, Anoka, MN (US)

(73) Assignee: SarTec Corporation, Anoka, MN (US)

( * ) Notice: Subject to any disclaimer, the term of this patent is extended or adjusted under 35 U.S.C. 154(b) by 1055 days.

(21) Appl. No.: 11/937,612

(22) Filed: Nov. 9, 2007

(65) Prior Publication Data

US 2008/0145457 A1 Jun. 19, 2008

Related U.S. Application Data

(60) Provisional application No. 60/865,007, filed on Nov. 9, 2006.

(51) Int. Cl.

| | |
|---|---|
| *A61K 36/8965* | (2006.01) |
| *A61K 36/48* | (2006.01) |
| *A61K 36/894* | (2006.01) |
| *A61K 36/82* | (2006.01) |
| *A61K 31/704* | (2006.01) |
| *A61K 36/185* | (2006.01) |
| *A61K 36/73* | (2006.01) |
| *A61K 36/88* | (2006.01) |
| *A61K 36/896* | (2006.01) |

(52) U.S. Cl.
CPC .............. *A61K 36/82* (2013.01); *A61K 31/704* (2013.01); *A61K 36/185* (2013.01); *A61K 36/48* (2013.01); *A61K 36/73* (2013.01); *A61K 36/88* (2013.01); *A61K 36/896* (2013.01)

(58) Field of Classification Search
None
See application file for complete search history.

(56) References Cited

U.S. PATENT DOCUMENTS

| | | | |
|---|---|---|---|
| 5,139,779 A * | 8/1992 | McNeff | ......................... 424/750 |
| 5,240,727 A | 8/1993 | McNeff | |
| 5,279,838 A | 1/1994 | McNeff | |
| 5,518,750 A | 5/1996 | McNeff | |
| 7,416,742 B2 | 8/2008 | McNeff et al. | |
| 2006/0024387 A1 | 2/2006 | McNeff et al. | |
| 2006/0073194 A1 | 4/2006 | Taylor, Jr. et al. | |
| 2007/0071849 A1 | 3/2007 | McNeff | |
| 2007/0243269 A1 | 10/2007 | McNeff et al. | |

FOREIGN PATENT DOCUMENTS

| | | | | |
|---|---|---|---|---|
| JP | 404365453 A | * | 12/1992 | ................ A23K 1/16 |
| JP | 2002284683 | * | 10/2002 | ............ C07D 211/60 |

OTHER PUBLICATIONS

Matsumoto et al. Pipecolic Acid Induces Apoptosis in Neuronal Cells. Brain Research. 980. 2003. pp. 179-184.*
Hussain Yusuf et al. Pipecolic Acid in Rumen Fluid and Plasma in Ruminant Animals. Animal Science Journal. 2003. 74, pp. 184-193.*
Lu et al. Alfalfa Saponins Affect Site and Extent of Nutrient Digestion in Ruminants. The Journal of Nutrition. 1987. pp. 919-927.*
Fujita et al. Determination of D- and L-Pipecolic Acid in Food Samples Including Processed Foods. Annals of Nutrition and Metabolism. 2003. 47; pp. 165-169.*
Wina et al. The Impact of Saponins or Saponin-Containing Plant Materials on Ruminat Production—A Review. J. Acric. Food Chem. 2005. 53. pp. 8093-8105.*
Hussain-Yusuf, Hazizul et al., "Pipecolic acid in rumen fluid and plasma in ruminant animals", *Anim. Sci. J.* (Jap.) 2003 , 74:187-193.
Hussain-Yusuf, Hazizul et al., "Quantitative studies of the in vitro production of pipecolic acid by rumen protozoa and its degradation by rumen bacteria", *Anim. Sci. J.* 2002 , 73: 485-495.
Matsumoto, Shinji et al., "Pipecolic acid induces apoptosis in neuronal cells", *Brain Res.* 2003 , 980: 179-184.
Muroya, Shinji et al., "Gamma aminobutyric acid regulates glucosensitive neuropeptide Y neurons in arcuate nucleus via A/B receptors", *Neuroreport* 2005 , 16(9): 897-901.
Navas-Camacho, Alberto et al., "Effect of reducing the rumen ciliate protozoa population by feeding saponin-containing plants on rumen function of sheep fed on wheat straw", *Arch. Latinoam. Prod. Anim.* 5 1997 , Supl. 1:98-101.
Struys, E. A. et al., "Enantiomeric analysis of D- and L-pipecolic acid in plasma using a chiral capillary gas chromatography column and mass fragmentography", *J. Inher. Metab. Dis.* 1999 , 22:677-678.
Takagi, T. et al., "Intracerebroventricular administration of GABA-A and GABA-B receptor antagonists attenuate feeding and sleeping-like behavior induced by L-pipecolic acid in neonatal chicks", *Neurosci. Res.* 2003 , 73: 270-275.
Takagi, Tomo et al., "Intracerebroventricular injection of pipecolic acid inhibits food intake and induces sleeping-like behaviors in the neonatal chick", *Neuroscience Letters* 2001 , 310: 97-100.

* cited by examiner

*Primary Examiner* — Chris R Tate
*Assistant Examiner* — Deborah Davis
(74) *Attorney, Agent, or Firm* — Pauly, DeVries Smith and Deffner, L.L.C.

(57) ABSTRACT

The present invention relates to methods and compositions for reducing L-pipecolic acid concentrations and/or effects in animals. In an embodiment, the invention includes a method of reducing plasma concentrations of L-pipecolic acid in animals including administering an effective amount of a composition including saponins. In an embodiment, the invention includes a method of reducing anorectic effects of L-pipecolic acid in animals including administering an effective amount of a composition including saponins. Other embodiments are also included herein.

9 Claims, No Drawings

METHODS AND COMPOSITIONS FOR REDUCING L-PIPECOLIC ACID EFFECTS IN ANIMALS

This application claims the benefit of U.S. Provisional Application No. 60/865,007, filed Nov. 9, 2006, the content of which is herein incorporated by reference.

FIELD OF THE INVENTION

The present invention relates to methods and compositions for reducing L-pipecolic acid concentrations and/or effects in animals.

BACKGROUND OF THE INVENTION

L-pipecolic acid (L-PIP) (CAS Reg. #535-75-1) is a non-protein amino acid that is widely distributed in higher and lower plants. L-PIP is also derived via lysine catabolism in many organisms.

L-PIP has anorectic (appetite reducing) effects in animals. As an example, it was shown that ICV injection of L-PIP inhibited food intake and induced sleep-like behavior in chicks (Takagi et al., Neurosci. Lett., 2001, 310:97-100). It is believed that L-PIP's anorectic effects are mediated by L-PIP's interaction with various molecular components in the brain such as neuropeptide Y (NPY). NPY is a 36-residue peptide neurotransmitter that is a potent stimulator of feeding. There is a natural afferent signal to the lateral hypothalamic area associated with NPY that results in appetite stimulation. It is believed that L-PIP interferes with this signal resulting in anorectic effects.

The anorectic effects of L-PIP are undesirable, particularly in cattle production due to lower feed intake resulting in lower weight gain and an increase in overall beef production costs. In dairy cattle the anorectic effects can lead to an increase in milk production costs. L-PIP may also cause other undesirable effects in the brain. For example, L-PIP is known to induce apoptosis in neuronal cells (Matsumoto, Brain Res., 2003, 980:179). High levels of L-PIP have also been associated with Zellweger syndrome, Refsum disease, and various peroxisomal disorders.

Therefore, a need exists for methods and compositions for reducing the effects of L-pipecolic acid.

SUMMARY OF THE INVENTION

The present invention relates to methods and compositions for reducing L-pipecolic acid concentrations and/or effects in animals. In an embodiment, the invention includes a method of reducing plasma concentrations of L-pipecolic acid in animals including administering an effective amount of a composition including saponins. In an embodiment, the invention includes a method of reducing anorectic effects of L-pipecolic acid in animals including administering an effective amount of a composition including saponins. In an embodiment, the invention includes a method for treating a peroxisomal disorder in an animal including administering an effective amount of a composition including saponins.

DETAILED DESCRIPTION OF THE INVENTION

L-PIP has anorectic effects in animals mediated by L-PIP's interaction with targets in the brain. Specifically, it has been shown that ICV injection of L-PIP inhibited food intake and induced sleep-like behavior in chicks (Takagi et al., Neurosci. Lett., 2001, 310:97-100). It is believed that L-PIP's anorectic effects involve γ-amino butyric acid (GABA) and neuropeptide Y (NPY).

γ-amino butyric acid (GABA) is a neurotransmitter that has been shown to have effects on feed intake. Early neurophysiological studies in the rat indicated that there is a possible relationship between L-PIP and GABA within the neurons of the lateral hypothalamic area (LHA; Takahama et al, 1982, as cited in Takagi et al., Neurosci. Lett., 2001, 310:97-100). Recently, it was shown that ICV injection of GABA-B receptor antagonists attenuated feeding and sleeping-like behavior induced by L-pipecolic acid (Takagi et al., J. Neurosci. Res., 2003, 73:270-275).

GABA has been shown to regulate glucosensitive neuropeptide Y containing neurons in the hypothalamic arcuate nucleus. Neuropeptide Y (NPY) is a 36-residue peptide neurotransmitter that is a potent stimulator of feeding. NPY containing neurons in the hypothalamic arcuate nucleus (ARC) are known to play a central role in the stimulation of feeding and anabolic metabolism (Muroya et al., Neuroreport, 2005, 16(9):897-901). It is believed that L-PIP interferes with the effects of NPY resulting in suppressed feeding behavior.

It has been demonstrated that rumen protozoa produce L-PIP and that rumen bacteria degrade L-PIP (Hussain-Yusuf et al., Anim. Sci. J. (Jap.), 2002, 73:485-495). However, based on rates of generation and degradation of L-PIP, it was concluded that: 1) L-PIP is absorbed by the host animal at a rate that is faster than it can be degraded by rumen bacteria, and 2) the majority of the L-PIP in the plasma of ruminants is of protozoal origin. This hypothesis was supported with data provided in a subsequent report in goats and cattle (Hussain-Yusuf et al., Anim. Sci. J. (Jap.), 2003, 74:187-193). Interestingly, those authors concluded that protozoan-generated L-PIP was "desirable because of its relaxing, stabilizing, and stress-reducing effects" upon animals housed in confinement. However, the authors did not measure feed intake in the animals or address the anorectic effects of L-PIP.

Beyond reduced feed intake, L-PIP may also cause other negative effects in the brain. For example, L-PIP is known to induce apoptosis in neuronal cells (Matsumoto, 2003, Brain Res., 980:179). Further, high levels of L-PIP have also been associated with Zellweger syndrome, Refsum disease, and various peroxisomal disorders in humans. Peroxisomal disorders are a group of congenital diseases characterized by the absence of normal peroxisomes in the cells of the body. Even where high levels of L-PIP are primarily due to metabolic defects, such as in many peroxisomal disorders, it is believed that reduction in absorbed L-PIP produced by protozoa may provide therapeutic benefits.

Embodiments of the invention include methods of reducing plasma levels of L-PIP. Plasma levels of L-PIP can be reduced and the anorectic effects of L-PIP can be mitigated by administration of saponins and/or saponin containing compositions. Saponins have antiprotozoal activity. Specifically, saponins can lyse protozoa through interactions with the cell walls of protozoa. Therefore, saponins can reduce populations of rumen protozoa that produce L-PIP, leading to a reduction in absorbed amounts of L-PIP and/or reduced plasma levels of L-PIP. Furthermore, protozoa prey upon bacteria in the rumen. Therefore, administration of saponins can lead to enhanced populations of rumen bacteria that degrade L-PIP, also resulting in a reduction in absorbed amounts of L-PIP and/or reduced plasma levels of L-PIP. Furthermore, since saponins are not toxic to most rumen bacteria (excepting methanogens) they do not reduce the overall bacterial population in the rumen.

In an embodiment, the invention includes a method of reducing plasma concentrations of L-pipecolic acid in animals including administering an effective amount of a composition including saponins. In an embodiment, the invention includes a method of reducing anorectic effects of L-pipecolic acid in animals comprising administering an effective amount of a composition including saponins. In an embodiment, the invention includes a method for treating a peroxisomal disorder in an animal including administering an effective amount of a composition including saponins.

In some embodiments, methods of the invention can include administering a composition including an effective amount of saponins to an animal in need thereof. It will be appreciated that there are various techniques that can be used to assess the plasma concentration of L-pipecolic acid of an animal. By way of example, in one approach, a blood sample can be drawn and then L-pipecolic acid concentration can be determined by using ion-exchange chromatography on an amino acid analyzer (such as a Biotronik LC 2000 or LC 6000 from Biotronik, Hamburg, Germany). As another example, L-pipecolic acid concentration can be determined using a chiral capillary gas chromatography column and mass fragmentography. See Struys and Jakobs, J. Inher. Metab. Dis., 1999, 22:677-78. In an embodiment of a method, a step of testing an animal for plasma concentration of L-pipecolic acid is included.

Methods and compositions of the invention can be used to treat various kinds of animals. By way of example, methods and compositions of the invention can be used to treat ruminants. Examples of animals that can be treated can include bovine, equine, ovine, porcine, and various species of fowl.

Saponins

Saponins are natural plant surfactants that occur in over 500 different plant species belonging to some 80 different families. Saponins occur naturally in many foods consumed by humans including soybeans, peas, spinach, beetroot and asparagus. They are generally recognized by their strong foaming action when placed in water, which has made them especially useful in the manufacture of foods, beverages, shampoos, wetting agents and pharmaceuticals.

Saponins are classified as surfactants because they have both lipophylic and hydrophilic "regions". Thus, the surfactant activity of saponins is a result of both fat-soluble and water-soluble moieties in the same molecule. The lipophylic region may be a steroid, triterpene or alkaloid, and is termed a sapogenin. The hydrophilic "region" contains one or more water-soluble carbohydrate side chains. *Yucca* derived saponins generally have steroidal sapogenins. Sarsasapogenin is the major sapogenin found in the *Yucca schidigera* plant. A sarsasaponin is a saponin including sarsasapogenin. Saponins have an antiprotozoal activity attributed to the saponin's ability to interact with cholesterol in protozoal cell membranes and cause cell lysis.

The structural complexity of saponins is derived largely from the carbohydrate portion of the molecule due to the many different types of possible side chain carbohydrates, such as glucose, xylose, galactose, pentose or methylpentose, which may have different connectivity and/or anomeric configuration.

Saponin-Containing Compositions

Saponins useful in the present invention can be extracted from plants of the family: Amaryllidaccae, genus: *Agave*, which grows extensively in the southwestern United States and in Mexico. Saponins useful in the present invention may also be extracted from plants of the family: Lillaecae, genus: *Yucca*, such as *Yucca schidigera*. Saponins may also be obtained from extracts of soybeans, fenugreek, peas, tea, yams, sugar beets, as well as from *Quillaja saponaria* bark. Saponins may be extracted from plant materials in accordance with techniques well-known by those of skill in the art.

The *Yucca* plant is a wide-ranging genus, which is part of the Century plant family, Aguavacea. Taxonomically there are 30 species within the *Yucca* genus, *schidigera* being one. *Yucca* plants thrive mainly in semi-arid climates such as are found in India, Angola, Italy, Southwest U.S., and Mexico to name a few.

In general, the extracts are considered safe for use in animal feeds and for human consumption. The EPA has ruled that *Yucca* extract is exempt from the requirement of a tolerance. In regards to toxicology, an acute oral gavage toxicity study performed on Sprague-Dawley derived rats was performed using a 70% *yucca* extract syrup. The LD50 for males was found to be greater than 5,000 mg/kg, and for females it was calculated to be greater than 500 mg/kg.

The typical saponin content that naturally occurs in *yucca* plants is from 0.1-2% saponins by weight. *Yucca* extracts can be derived by extracting *yucca* powder with an aqueous solution that may or may not contain some fraction of organic solvent such as methanol, ethanol, propanol, butanol, or the like. Commercially available *Yucca* extracts can have a total solids content usually in the range from 5-50%. The saponin content of a typical 50 brix (50% solids by weight) *yucca* extract is usually in the range of about 1-2% saponins by weight as measured by HPLC analysis. Another method of measuring total saponin content is the extraction of all soluble components into a butanol extract followed by gravimetric analysis of the compounds dissolved in the butanol fraction. Measuring saponin content by the butanol extract method typically results in higher numbers than the more advanced HPLC method. Accordingly, the typical 50 brix (50% solids by weight) *yucca* extract is usually in the range of about 5-20.0% saponins content by weight as measured by the butanol extract method.

In an embodiment, the saponin containing composition used in accordance with the invention comprises at least 0.1% by weight saponins as measured by HPLC. In an embodiment, the saponin containing composition used in accordance with the invention comprises at least 0.5% by weight saponins as measured by HPLC. In a particular embodiment, the saponin containing composition used in accordance with the invention comprises at least 1.0% by weight saponins as measured by HPLC. It is believed that the effects of the composition are related to the total amount of saponins present. Thus, one of skill in the art will appreciate that if a certain amount of saponins is desired it can be achieved either through varying the volume of a certain concentration composition administered, varying the concentration of a certain volume of a composition, or both.

Exemplary liquid solutions containing saponins are available commercially and sold under the trademarks SARTEMP®, SARSTART®, SARSTART® PRO, SARSTART® LSC, and SARSTART® PLUS by SarTec Corporation of Anoka, Minn. These solutions are prepared by blending an aqueous extract of the plants of the family: Lillaecae, genus: *Yucca*, or other appropriate *Yucca* plants with antifreeze agents such as calcium chloride, propylene glycol, and the like, to depress the freezing point to approximately −30° F. These liquid solutions may also comprise a variety of other components. By way of example, SARSTART® PLUS can contain the following ingredients: water, propylene glycol, *Yucca schidigera* extract, vitamin E (as di-alpha-tocopheryl acetate), vitamin A propionate, vitamin A palmitate, vitamin B1, vitamin B2, vitamin B6, vitamin B12, D-Activated animal sterol (source of Vitamin D3), naturally occurring organisms, dried egg solids, dried casein, and dried whey. The physical and chemical characteristics of SARSTART® PLUS are as follows: Boiling Point: 240 F; Specific Gravity: 1; Melting Point: −20 F; Solubility in Water: Miscible; Appearance and Odor: Dark brown liquid with a mild odor and a slightly acid taste. Saponin containing compositions can also be formulated as dry powder. Such dry formulations are available commercially (SARSTART® D, SARSTART® DSC, SarTec Corporation, Anoka, Minn.).

Dosing of Saponin Compositions:

Saponin containing compositions in accordance with the invention may be in liquid or dry forms. By way of example, a *yucca* containing plant extract may be dried into a powder form. In this form, the *yucca* containing composition may be administered to an animal as a pill or bolus, gel, paste, or mixed in with other components such as a feed ration. Saponin containing plant extract may also be in a solution with an amount of a carrier liquid such as water. In this form, the saponin containing composition may be administered to an animal as a liquid drench.

Saponin containing compositions may be administered to animals daily in equal amounts. By way of example, animals may be dosed with 100 ml of a liquid composition comprising about 0.1 wt. % saponins. In some embodiments, a single larger dose may be given initially followed by smaller daily doses thereafter. For example, a single larger dose can be administered after animals are first discovered to have elevated plasma levels of L-pipecolic acid. The single larger dose can be administered as a bolus. A smaller daily dose may be administered after the larger dose and throughout the treatment phase. In an embodiment, the treatment phase lasts at least 28 days. In an embodiment, the treatment phase lasts for at least 60 days. In an embodiment, the smaller daily dose may be administered with a daily feed ration.

In an embodiment of the invention, the single larger dose, or initiation dose, is larger than each of the smaller daily doses, or maintenance doses. In an embodiment the initiation dose is at least 3 times larger than the daily dose. In an embodiment, the initiation dose is at least 5 times larger than the daily dose. In a particular embodiment, the initiation dose is at least 15 times larger than the daily dose.

In the life cycle of animals, such as cattle, there are times when the animal fasts. For example, the animal may fast while being shipped to a feedyard or the animal may fast while having a calf. When the animal is fasting, there is no food source for bacteria in the rumen and thus bacterial numbers go down while protozoan numbers go up. For this reason, it is believed that fasting can lead to increased levels of L-pipecolic acid. Administration of a saponin containing composition after a period of fasting can counteract these effects. In an embodiment of the invention, the administration of a saponin containing composition is initiated after a period of fasting.

The present invention may be better understood with reference to the following examples. These examples are intended to be representative of specific embodiments of the invention, and are not intended as limiting the scope of the invention.

EXAMPLES

Example 1

Effect of Saponins on Plasma Concentrations of L-Pipecolic Acid

A test herd of dairy cattle is divided into a treatment group and a control group. Measurements of plasma L-pipecolic acid concentrations are taken on day 0 for both groups. The treatment group is administered a 100 ml dose of a saponin-containing composition every day for a treatment period. Daily feed intake (dry matter basis) for both groups is monitored. The plasma concentrations of L-pipecolic acid are measured on a daily basis. The treatment group shows a reduction in plasma L-pipecolic acid concentrations and greater feed intake.

Example 2

Effect of Saponins on Plasma Concentrations of L-Pipecolic Acid in Post-Fasting Animals A test herd of beef cattle is divided into a treatment group and a control group. Both groups of cattle are fasted for a period of time. Measurements of plasma L-pipecolic acid concentrations are taken both before and after fasting for both groups. The treatment group is administered a 100 ml dose of a saponin-containing composition every day for a treatment period. During the treatment period, both groups are feed ad libitum. Daily feed intake (dry matter basis) for both groups is monitored. The plasma concentrations of L-pipecolic acid are measured on a daily basis. The treatment group shows a greater reduction in average plasma L-pipecolic acid concentration and a more rapid onset of increased feed intake in comparison to the control group.

The invention has been described with reference to various specific and preferred embodiments and techniques. However, it should be understood that many variations and modifications may be made while remaining within the spirit and scope of the invention.

We claim:

1. A method of reducing plasma concentration of L-pipecolic acid in a ruminant comprising:
    testing ruminants for plasma concentration levels of L-pipecolic acid;
    selecting ruminants that have an elevated plasma concentration of L-pipecolic acid;
    administering a composition comprising an effective amount of saponins to the selected ruminants;
    wherein said administering is performed after a period of fasting by the selected ruminants, and wherein said administering causes bacterial numbers to decrease and protozoan numbers to increase in the selected ruminants.

2. The method of claim 1, wherein the saponins are sarasaponins.

3. The method of claim 1, the composition comprising at least 0.1% by weight of saponins.

4. The method of claim 1, wherein the ruminants are bovine.

5. The method of claim 1, wherein the saponins are obtained from an extract of one or more plants selected from the group consisting of *Yucca, Agave, Quillaja*, Fenugreek, tea, soybeans, peas, yams, and sugar beets.

6. The method of claim 1, wherein the saponins are obtained from a *Yucca* extract.

7. The method of claim 1, wherein said administering is performed daily for at least 28 days.

8. The method of claim 1, wherein said administering is performed after the ruminants are shipped to a feedyard.

9. The method of claim 1, wherein said administering is performed after the ruminants birth calves.

* * * * *